United States Patent [19]

Peterson et al.

[11] 4,307,250

[45] Dec. 22, 1981

[54] AMINES VIA THE AMINATION OF OLEFINS

[75] Inventors: John O. H. Peterson, North Windham, Me.; Howard S. Fales, West Reading, Conn.

[73] Assignee: Air Products and Chemicals, Inc., Allentown, Pa.

[21] Appl. No.: 148,352

[22] Filed: May 9, 1980

[51] Int. Cl.$^3$ ............................................. C07C 91/02
[52] U.S. Cl. ................................... 564/445; 564/485
[58] Field of Search ............................... 564/445, 485

[56] References Cited

U.S. PATENT DOCUMENTS

| | | | |
|---|---|---|---|
| 1,894,792 | 1/1933 | Sehlecht et al. | 252/455 UX |
| 2,381,709 | 8/1945 | Apgar et al. | 260/464 |
| 2,392,107 | 1/1946 | Teter | 252/207 |
| 2,417,892 | 3/1947 | Teter | 564/485 X |
| 2,422,631 | 6/1947 | Olin et al. | 260/583 |
| 2,422,632 | 6/1947 | Olin et al. | 260/561 |
| 2,479,879 | 8/1949 | Teter | 564/485 X |
| 2,574,693 | 11/1951 | Engel et al. | 564/445 |
| 2,623,061 | 12/1952 | Teter | 564/485 X |
| 2,658,041 | 11/1953 | Teter et al. | 252/457 |
| 3,013,983 | 12/1961 | Breck et al. | 252/455 |
| 3,071,524 | 1/1963 | Schutze et al. | 204/154 |
| 3,369,019 | 2/1968 | Hamilton et al. | 260/268 |
| 3,412,158 | 11/1968 | McClain | 564/485 |
| 3,597,483 | 8/1971 | Haarer et al. | 564/445 |
| 4,205,012 | 5/1980 | Parker et al. | 260/583 J |

OTHER PUBLICATIONS

Molecular Sieve Catalysts, "Chemical Week, " pp. 78–85, 11/14/64.
"Wissenschaftliche Zeitschrift", 5, pp. 263–267, (1963).
FDR Application, I 74946 IVd/120, 3/23/44.
Doklady Akad. Nauk SSSR, 125, No. 4, 829–830, (1959).

*Primary Examiner*—Paul F. Shaver
*Attorney, Agent, or Firm*—Russell L. Brewer; James C. Simmons; E. Eugene Innis

[57] ABSTRACT

This invention relates to an improvement in the vapor phase catalytic production of an amine by the reaction of a mixture comprising an olefin having from 2 to 8 carbon atoms and ammonia or ammonia type compound. The improvement which provides for high selectivity to the amine resides in the use of an alumino silicate as the catalyst.

23 Claims, No Drawings

AMINES VIA THE AMINATION OF OLEFINS

BACKGROUND OF THE INVENTION

1. Field of the Invention

This invention relates to a process for producing amines by the reaction of ammonia or ammonia type compound with an olefin.

2. Description of the Prior Art

The earliest work relating to the manufacture of amines by the amination of olefins particularly ethylamines by the amination of ethylene, appears to have been done by Teter et al. as noted in U.S. Pat. Nos. 2,623,061; 2,479,879; 2,417,892; 2,381,470, 2,658,041; 2,381,709; 2,392,107 and 2,398,899. These patents show that ammonia can be made to react with olefins, e.g. ethylene to produce amine. As noted by others through improvements in the process, substantial quantities of polyamines and polyolefins were produced by the Teter et al catalyst which is a metal supported on a spinel type support, silica and diatomaceous earth and the like.

Olin et al. in U.S. Pat. Nos. 2,422,631 and 2,422,632, discloses a process for producing amines and amides by the reaction of a monounsaturated olefin, carbon monoxide and an amine or ammonia. The catalyst used is a combination of a dehydrating and a hydrogenation catalyst, e.g. nickel and activated alumina, copper and silica gel, etc.

Whitman, U.S. Pat. No. 2,501,556 discloses a liquid phase reaction of ammonia and ethylene in the presence of an alkali metal catalyst to form ethylamine.

McClain, U.S. Pat. No. 3,412,158 discloses a gas phase process for producing primary alkyl amines from low molecular weight olefins and ammonia by carrying out the gas phase process in the presence of a noble metal containing catalyst at temperatures of from 90°–175° C., at pressures of from atmospheric to 2,000 psig.

SUMMARY OF THE INVENTION

This invention relates to an improved process for the preparation of amines by the vapor phase catalytic reaction of an olefin having from 2 to 8 carbon atoms and ammonia or a primary or secondary amine. In the basic process the olefin is reacted at a temperature and pressure sufficient to effect formation of the amine, but controlled to prevent polymer formation. The improvement generally resides in the use of (a) a temperature from 200°–450° C.,
(b) a pressure of from 300–6,000 psig and
(c) an alumino silicate, e.g. a zeolite, catalyst.

There are several advantages associated with the invention as compared to prior art processes. These advantages include:

an ability to produce amines in high selectivity with respect to polyamines, e.g. greater than about 80% without producing substantial by-products, e.g. polymers in the form of polyolefins. The production of polymers has been a serious problem with many of the prior art processes;

an ability to use a gas phase reaction which permits high production rate in producing amines;

an ability to reduce the amount of by-product in the form of by-product nitrogen compounds (nitriles) as compared to prior art processes; and an ability to obtain moderate conversion of olefin to amines by virtue of the use of the particular catalyst and conditions employed.

DESCRIPTION OF THE PREFERRED EMBODIMENT

Olefins having from 2 to 8 carbon atoms in the structure can be converted by vapor phase amination to the amine. The olefins can be mono or polyunsaturated, e.g. a diene. However, a monounsaturated olefin which is an alpha-beta unsaturated aliphatic olefin is preferred. Dienes, particularly conjugated dienes, have a tendency to polymerize. Examples of olefins suited for producing amines by this process are ethylene, propylene, butylene, isobutylene, pentene, hexene, cyclohexene, cyclopentadiene and butadiene, of these the $C_2$ to $C_4$ olefins are preferred in practicing the invention and these would include ethylene, propylene, and the butenes.

In the amination of the olefins, and ammonia or an ammonia type compound, i.e. a primary or secondary amine can be used as the reactant. If one uses a primary or secondary amine as the reaction item, secondary and tertiary amines are formed as product. Suitable primary and secondary amines can be represented by the formulas $RNH_2$ and $(R)_2NH$ where each R is a hydrocarbon group having from 1–6 carbon atoms in the structure. Examples of amines include methyl amine, dimethylamine, mono an di-n-propylamine, cyclohexylamine, and the like. Lower alkyl amines are preferred.

In the process, an ammonia type compound is reacted with the olefin at temperatures broadly from about 200°–450° C., but preferably at temperatures of about 300°–400° C. Lower temperatures result in lower conversion and higher temperatures result in lower selectivity which generally appears in the form of polymer or nitrile formation.

Pressures suited for practicing the invention are from about 300–6,000 psig with preferred pressures of from about 600–1100 psig. Generally, pressures lower than about 600 psig result in poor conversion of the olefin to amine. On the other hand, as the pressure is increased above about 1500 psig conversion is increased only slightly. However, selectivity to the amine decreases particularly when conjugated dienes such as butadiene are used as the reactants. In order to minimize the recovery problems associated with separating the amine from the reactants and other by-products, higher conversions can be waived and pressures of from about 600–1100 psig used as this permits extremely high selectivities, e.g. greater than 95%.

Another important variable in the gas phase amination of the olefin is the mole ratio of ammonia to olefin in the feed. Generally, the mole ratio can be from about 0.2–20 moles ammonia per mole of olefin with preferred ranges of from about 1–4 to 1. Mole ratios higher than about 10:1 of course require greater energy expenditure to handle the larger quantities of gas that pass through the reactor, and there seems to be no significant advantage in terms of increased selectivity or conversion at these higher ratios of ammonia to olefin. On the other hand, as the concentration of ammonia to olefin falls below about 0.2:1, there is a loss of selectivity to the amine.

The gas hourly space velocity (GHSV) which has units of volume of gas per volume of catalyst in unit time i.e. (cc gas at STP)/(cc catalyst hours$^{-1}$). The gas hour space velocity can be from about 500–5,000 with a preferred range being from about 750–2,000. As the space velocity is increased toward the upper end of the range, conversion generally falls dramatically, particularly above about 3,000. On the other hand, as the space velocity approaches the lower level of 500, selectivity decreases as by-products form. Typically, conversions of from about 3-20% are achieved at space velocities of about 500-3,000.

One of the important factors in achieving the results of high selectivity to amines without the concomitant production of substantial amounts of polymers, e.g. polyethylene or other by-products as encountered in the prior art processes is in the use of alumino silicates, e.g. various ion exchanged zeolites as the catalyst. Various ions can be incorporated into the synthetic crystalline alumino silicates which enhance the activity of the resultant catalyst. It is believed the acidity of the catalyst as well as the resistance of the ion to reduction to the metal form plays an important role in the catalyst activity and selectivity. The acidity is provided by the metallic ions. The reduction of the metal ions to the metal destroys the acidity and this form then catalyzes the dehydrogenation of the amine to nitriles. Trivalent ions and particularly the rare earth metals, i.e. lanthanum, neodymium, praseodymium, are well suited. Other trivalent ions include iron, aluminum, chromium and rhenium. Divalent ions often result in poorer conversion than the rare earth trivalent ions however, selectivity is good. Divalent ions include calcium, magnesium and copper. Zinc, although a divalent ion, generally effects dehydrogenation of the amine to the nitrile, but it is operable. Monovalent ions, i.e. hydrogen, sodium and ammonium ions are also effective for the catalyst. However, sodium and other alkali metals result in lower conversions than the hydrogen form. As is known the hydrogen form can be prepared from the ammonium form and for purposes herein is referred to as the hydrogen form. The preferred metal ions for the exchanged zeolites are lanthanum and hydrogen as these provide good yields, good selectivity and good catalyst life.

Synthetic crystalline alumino silicates generally are present in the sodium form and, of course, the sodium form can be replaced by washing the zeolite with a metal salt solution and effecting ion exchange with the sodium. The hydrogen form can be obtained by washing with an acid or an ammonium salt solution and heating to drive off ammonia.

The term zeolite, as used herein, refers to the synthetic, crystalline alumino silicate of the molecular sieve type. They are formed by the reaction of sodium aluminate and colloidal silica. These zeolites are well known and are described in U.S. Pat. Nos. 3,130,007; 2,882,244 and 3,130,006 and incorporated by reference. These references primarily relate to zeolites of the X and Y type, the Y type having a silica to alumina ratio of at least 3.5. Other types such as the A, and mordenites can also be used in the gas phase amination of olefins described here. Zeolite Y which is described in U.S. Pat. No. 3,130,007 provides excellent results.

Another form of alumino silicate is silica-alumina where the silica content is from about 10-50% by weight. This form of silica-alumina is distinguished from the zeolite in that it is not in the crystalline form. Generally, conversion is lower with the noncrystalline alumino-silicates than with the zeolite, particularly those exchanged with a trivalent rare earth metal ion.

The following examples are provided to illustrate preferred embodiments of the invention and are not intended to restrict the scope thereof.

EXAMPLE 1

The reactor used consisted of a 36 inch tube having an internal diameter of 0.815 inches. A thermowell of one-quarter inch outside diameter was axially extended up from the bottom portion of the reactor. The catalyst pellets, as specified, occupied the lower half of the reactor. The upper part of the reactor was filled with inert packing, one-quarter inch unglazed porcelain berl saddles. The saddle served as a preheating and mixing device. Each section of the reactor, i.e. the preheater and the catalyst bed, was equipped with an external electric heater which was independently controlled to maintain temperature.

The reactor product was sampled by diverting the product stream to a scrubber containing an icewater mixture. A material immiscible with water remained as an upper layer and decanted or was condensed in a dry ice-cooled trap. Noncondensibles were measured by a wet test gas meter. The products were then analyzed by vapor-phase chromatography.

Table 1 represents the results of amination of various olefins under various conditions, the conditions being specified in the table. Catalyst SK-500 is a pelleted rare earth lanthanum exchanged zeolite Y sold by the Union Carbide Company. G-980 is a silica-alumina catalyst containing 13-25% alumina.

With respect to amine formation in Table 1, employing a toluene extraction method of analysis selectivity to monoethylamine was 79% in Run 1, and 68% in run 2, runs 3 and 4 produced an 87-92% monoisopropylamine. Run 5 and 10 resulted in conversions to 100% 2-aminobutane and cyclohexylamine respectively.

Subsequent analysis using distillation techniques indicated about an 80% selectivity to amines instead of the 95-100% level reported in Run 1. The concentration of monoethylamine was about 61%. This trend would be expected to be carried along in other runs. The toluene extraction method may have resulted in lower polymer analysis, however, yield errors may have resulted in the distillation technique. Nonetheless, both analytical techniques show high selectivity to amines.

TABLE 1

| | | Amination of Olefins Under Various Operating Conditions | | | | | | |
|---|---|---|---|---|---|---|---|---|
| Run | Olefin | Catalyst | T,°C. | Psig | GHSV | $NH_3$/Olefin Mole Ratio | % Conv. | To Amines % Selec. | Sp-Time Yield lb./hr./ft.$^3$ of catalyst |
| 1 | Ethylene | SK-500 | 386 | 3000 | 3000 | 2.3 | 13.2 | 95 | 13.8 |
| 2 | Ethylene | " | 403 | " | " | " | 20.6 | 85 | 18.7 |
| 3 | Propylene | " | 367 | " | 3400 | 1.0 | 6.2 | 91 | 15.5 |
| 4 | Propylene | " | 383 | " | 3100 | 2.8 | 8.4 | 93 | 10.3 |
| 5 | Propylene | G-980 | 446 | 2000 | 3000 | 4.1 | 6.2 | 100 | 6.0 |
| 6 | Butene-2 | SK-500 | 374 | 2000 | 3300 | 5.4 | 3.7 | 100 | 3.9 |
| 7 | Butene-1 | " | 377 | 2000 | 3300 | 5.5 | 5.4 | 100 | 5.3 |
| 8 | Isobutylene | " | 313 | 2000 | 3100 | 2.7 | 6.5 | 100 | 11.1 |

TABLE 1-continued

Amination of Olefins Under Various Operating Conditions

| Run | Olefin | Catalyst | T,°C. | Psig | GHSV | NH₃/Olefin Mole Ratio | % Conv. | To Amines % Selec. | Sp-Time Yield lb./hr./ft.³ of catalyst |
|---|---|---|---|---|---|---|---|---|---|
| 9 | Isobutylene | " | 278 | 2000 | 2900 | 1.3 | 6.1 | 100 | 16.0 |
| 10 | Cyclohexene | " | 335 | 3000 | 3000 | 4.8 | 10.0 | 100 | 14.3 |
| 11 | Propylene | " | 400 | 4000 | 3100 | 1.0 | 8.7 | 93 | 20.5 |

EXAMPLE 2

The procedure of Example 1 run 3 was repeated except for the variation in temperature, pressure and other process conditions as specified in Table 2. The catalyst used was SK-500.

The results show that conversion dropped with decreasing temperature but selectivity to the amine increased. For propylene it wasn't until reactor temperatures reached about 410° C. that polymerization started to occur.

TABLE 2

Direct Amination of Propylene at 4000 psig Pressure
Changes in Product Distribution with Temperature

| Temperature, °C. | 413 | 400 | 383 | 360 |
|---|---|---|---|---|
| NH₃/Propylene (molar ratio) | 0.9 | 1.0 | 0.9 | 0.9 |
| Space velocity, hr⁻¹ | 3000 | 3100 | 3100 | 3100 |
| Propylene Conversion, % | 9.6 | 8.7 | 7.8 | 4.5 |
| Selectivity, % | | | | |
| Isopropylamine | 68 | 88 | 91 | 93 |
| Unknown | 9 | 7 | 3 | 4 |
| Diisopropylamine | 4 | 5 | 6 | 3 |
| Polymers | 19 | 0 | 0 | 0 |
| Space-time yields, lb./hr./cu.ft. of catalyst | | | | |
| Isopropylamine | 17.1 | 19.6 | 18.9 | 11.0 |
| Diisopropylamine | 0.8 | 0.9 | 1.0 | 0.3 |
| TOTAL | 17.9 | 20.5 | 19.9 | 11.3 |

EXAMPLE 3

Another series of amination reactions were carried out using a reactor consisting of a 316 stainless steel tubing 9 inches long of ¾" outside diameter and ½" inside diameter. The stainless steel reactor was mounted inside a close fitting block of Inconel metal which was instrumented for temperature control. A thermowell extending axially through the reactor was used to measure reactor temperature.

The catalyst volume for the reactor was approximately 30 cubic centimeters and the catalyst was held in place by a quartz wool plug. The catalysts were sieved to pass through a U.S. standard sieve size 12 but retained on an 18 mesh sieve.

Tables 3 and 4 represents results for various olefins, catalysts and reactor conditions.

Table 3 shows that a hydrogen form of mordenite is effective for producing monoamines from ethylene and propylene in high yield. Very few byproducts are formed at 750 psig and temperatures below about 380° C. As with the previous examples conversion increases with temperature but selectivity decreases at the upper end of the temperature range e.g. 400° C. Even so, selectivity is much higher than with the conventional catalysts on silica.

As compared to Example 1, amine selectivity is higher. Although a different analytical technique was used, the major contribution to increased selectivity was the use of lower pressures. Olefins are less susceptible to polymerization at lower pressures.

TABLE 3

AMINATION OF ETHYLENE AND PROPYLENE

| | | | | | | NH₃/Olefin | | % Selectivity | | |
|---|---|---|---|---|---|---|---|---|---|---|
| Run | Olefin | Catalyst | T, °C. | Psig | GHSV | Mole Ratio | % Conv. | Mono Amines | Diamine | Other |
| 1 | Ethylene | H Mordenite Zeolite | 340 | 750 | 1960 | 3.9:1 | 3.6 | 98 | 2 | — |
| 2 | " | H Mordenite Zeolite | 350 | 750 | 1960 | 3.9:1 | 4.7 | 97 | 3 | — |
| 3 | " | H Mordenite Zeolite | 360 | 750 | 1960 | 3.9:1 | 7.5 | 97 | 3 | — |
| 4 | " | H Mordenite Zeolite | 370 | 750 | 1960 | 3.9:1 | 9.4 | 91 | 8.7 | 0.3 |
| 5 | " | H Mordenite Zeolite | 380 | 750 | 1960 | 3.9:1 | 12.6 | 89 | 10.4 | 0.6 |
| 6 | " | H Mordenite Zeolite | 390 | 750 | 1960 | 3.9:1 | 14.0 | 86 | 11 | 3 |
| 7 | " | H Mordenite Zeolite | 400 | 750 | 1960 | 3.9:1 | 14.0 | 88 | — | 12 |
| 8 | Propylene | H Mordenite Zeolite | 300 | 750 | 1960 | 4.0:1 | .3 | 100 | — | — |
| 9 | " | H Mordenite Zeolite | 310 | 750 | 1960 | 4.0:1 | 4.7 | 100 | — | — |
| 10 | " | H Mordenite Zeolite | 320 | 750 | 1960 | 4.0:1 | 6.8 | 100 | — | — |
| 11 | " | H Mordenite Zeolite | 330 | 750 | 1960 | 4.0:1 | 9.1 | 100 | — | — |
| 12 | " | H Mordenite Zeolite | 340 | 750 | 1960 | 4.0:1 | 11 | 99 | — | — |
| 13 | " | H Mordenite Zeolite | 350 | 750 | 1960 | 4.0:1 | 11.3 | 98.6 | — | — |

TABLE 4
AMINATION OF PROPYLENE

| Run | Olefin | Catalyst | T, °C. | Psig | GHSV | NH₃/Olefin Mole Ratio | % Conv. | % Selectivity Mono Amines | Diamine | Other |
|---|---|---|---|---|---|---|---|---|---|---|
| 1 | Propylene | H Mordentite | 330 | 750 | 2340 | 2:1 | 6.7 | 94.8 | 3.6 | 1.6 |
| 2 | " | " | 340 | 750 | 2340 | 2:1 | 8.4 | 93 | 4.3 | 2.1 |
| 3 | " | " | 350 | 750 | 2340 | 2:1 | 8.7 | 93 | 3.1 | 2.4 |
| 4 | " | Lanthanum Zeolite Y | 340 | 750 | 974 | 4:1 | 13.7 | 97 | 1.8 | 1.2 |
| 5 | " | Lanthanum Zeolite Y | 350 | 750 | 974 | 4:1 | 13.3 | 97 | — | 3 |
| 6 | " | Lanthanum Zeolite Y | 360 | 750 | 974 | 4:1 | 15 | 90 | — | 7.8 |
| 7 | " | Lanthanum Zeolite Y | 330 | 750 | 1950 | 4:1 | 8 | 100 | — | — |
| 8 | " | Lanthanum Zeolite Y | 340 | 750 | 1950 | 4:1 | 11.6 | 100 | — | — |
| 9 | " | Lanthanum Zeolite Y | 370 | 750 | 1950 | 4:1 | 14.9 | 94 | 1.6 | 23 |
| 10 | " | Lanthanum Zeolite Y | 290 | 1100 | 1950 | 4:1 | 1.0 | 100 | — | — |
| 11 | " | Lanthanum Zeolite Y | 330 | 1100 | 1950 | 4:1 | 8.04 | 96.3 | 2.5 | — |
| 12 | " | Lanthanum Zeolite Y | 350 | 1100 | 1950 | 4:1 | 10.8 | 95.5 | 1.8 | — |

EXAMPLE 4

EXAMPLE 4

The procedure of Example 3 was repeated except for the changes as noted.

Runs 1 and 2 used a mixture of rare earth metals as the exchange ion. The rare earth metal mixture contained 59% lanthanum, 15% cerium, 7% praseodymium, and 19% neodymium by weight. Further the reactor contained only 6 cc of catalyst, the reactor being a ⅜ inch O.D. 14 inch I.D. stainless steel tube. Other reactor conditions as noted in the previous examples remained the same.

Runs 3–7 used a silica-alumina catalyst consisting of 15% silica by weight.

Table 5 gives the operating conditions and results.

Runs 1 and 2 show slightly lower conversions and selectivity than the total lanthanum exchanged zeolite of Table 4 but it would appear that any of the rare earth metal ions are effective in combination with the zeolite support to produce amines.

Silica-alumina when used as a catalyst gave poor conversions over the complete temperature range. However, selectivity was high.

In Tables 3, 4, and 5 it is shown that a rare earth ion exchanged zeolite, namely a lanthanum exchanged zeolite Y, is more active than the other catalysts in the series. Conversions are 3–4% higher on the average under similar conditions and yet there is excellent selectivity.

EXAMPLE 5

The procedure of Example 3 was used except for the change in catalysts and reaction conditions. These are

TABLE 5
AMINATION OF PROPYLENE

| Run | Olefin | Catalyst | T, °C. | Psig | GHSV | NH₃/Ethylene Mole Ratio | % Conv. | % Selectivity Mono Amines | Diamine | Other |
|---|---|---|---|---|---|---|---|---|---|---|
| 1 | Propylene | Rare Earth Zeolite Y | 340 | 750 | 1950 | 4:1 | 9.8 | 97 | 1.1 | — |
| 2 | " | Rare Earth Zeolite Y | 350 | 750 | 1950 | 4:1 | 10.9 | 96 | 0.8 | 1.3 |
| 3 | " | Silica-Alumina | 325 | 750 | 1950 | 4:1 | 0.2 | 100 | — | — |
| 4 | " | " | 380 | 750 | 1950 | 4:1 | 1.59 | 100 | — | — |
| 5 | " | " | 400 | 750 | 1950 | 4:1 | 2.8 | 100 | — | — |
| 6 | " | " | 430 | 750 | 1950 | 4:1 | 3.7 | 91 | 5 | — |
| 7 | " | " | 450 | 750 | 1950 | 4:1 | 3.2 | 81 | 19 | — | specified in Table 6.

TABLE 6
AMINATION OF OLEFIN

| Run | Olefin | Catalyst | T, °C. | Psig | GHSV | NH₃/Olefin Mole Ratio | % Conv. | % Selectivity Mono Amines | Diamine | Other |
|---|---|---|---|---|---|---|---|---|---|---|
| 1 | Isobutylene | H Mordenite | 300 | 750 | 1960 | 3.95:1 | 15 | 72 | — | 29 |
| 2 | " | " | 310 | 750 | 1960 | 3.95:1 | 18 | 49 | — | 51 |
| 3 | " | " | 320 | 750 | 1960 | 3.95:1 | 23 | 34 | — | 65 |
| 4 | " | " | 310 | 750 | 1960 | 3.95:1 | 26 | 24 MEA | — | 76 |
| 5 | Ethylene | Lanthanum Zeolite Y | 350 | 750 | 1960 | 4:1 | 3.9 | 100 | — | — |
| 6 | " | Lanthanum Zeolite Y | 380 | 750 | 1960 | 4:1 | 9.2 | 94 | 6 | 3 |

TABLE 6-continued

AMINATION OF OLEFIN

| Run | Olefin | Catalyst | T, °C. | Psig | GHSV | NH₃/Olefin Mole Ratio | % Conv. | % Selectivity Mono Amines | Diamine | Other |
|---|---|---|---|---|---|---|---|---|---|---|
| 7 | " | Lanthanum Zeolite Y | 390 | 750 | 1960 | 4:1 | 11.3 | 86 | 7 | 7 |
| 8 | Ethylene | Na Zeolite Y | 350 | 750 | 1960 | 4:1 | 0.5 | 100 | — | — |
| 9 | " | " | 380 | 750 | 1960 | 4:1 | 1.3 | 100 | — | — |
| 10 | " | " | 400 | 750 | 1960 | 4:1 | 1.9 | 78 | — | — |
| 11 | Ethylene | NH₄ Zeolite Y | 380 | 750 | 1960 | 4:1 | 8.8 | 89 | 7 | 3 |
| 12 | " | " | 385 | 750 | 1960 | 4:1 | 9.3 | 87 | 7 | 6 |
| 13 | " | " | 390 | 750 | 1960 | 4:1 | 9.9 | 84 | 0 | 7 |
| 14 | Ethylene | Zinc Zeolite Y | 350 | 750 | 1960 | 4:1 | 2.0 | 11 | — | 89 |
| 15 | Ethylene | Copper Zeolite Y | 350 | 750 | 1960 | 4:1 | 2.1 | 100 | — | — |
| 16 | " | " | 360 | 750 | 1960 | 4:1 | 2.9 | 94 | — | 6 |
| 17 | " | " | 370 | 750 | 1960 | 4:1 | 4.1 | 88 | — | 12 |
| 18 | Ethylene | Lanthanum Zeolite X | 350 | 750 | 1960 | 4:1 | 1 | 100 | — | — |
| 19 | " | Lanthanum Zeolite X | 380 | 750 | 1960 | 4:1 | 3.0 | 100 | — | — |
| 20 | " | Lanthanum Zeolite X | 400 | 750 | 1960 | 4:1 | 5.5 | 96.5 | 2.5 | — |
| 21 | " | Lanthanum Zeolite | 420 | 750 | 1960 | 4:1 | 8.3 | 89 | 4.4 | 6.4 |

With respect to Table 6 isobutylene in contrast to butene results in a high proportion of t-butyl amine. In addition there appeared to be cracking of the molecule which results in a larger percentage of byproducts. On this basis alkyl substituted olefins would be expected to give a wider variety of products. For best results, in terms of selectivity, then the olefin should be a straight chain olefin having alpha-beta unsaturation.

As to the various ion exchanged zeolite catalysts, the sodium, zinc and copper form resulted in poorer conversion than the lanthanum ion exchanged or hydrogen exchanged form. However the ammonium form is converted to the hydrogen form and gives good conversions to monoethylamine (MEA) with slightly lower selectivity than the lanthanum exchanged zeolite.

What is claimed is:

1. In a vapor phase catalytic amination process for the production of amines from a reaction mixture comprising an olefin having from 2-8 carbon atoms and a nitrogen compound selected from the group consisting of ammonia and primary and secondary amines at a temperature and pressure sufficient for effecting formation of said amine the improvement which comprises:
   (a) employing a temperature and pressure sufficient to form said amine, but insufficient for forming substantial polymerization of the olefin; and
   (b) employing as said catalyst an alumino silicate.

2. The process of claim 1 wherein said alumino silicate is a synthetic crystalline alumino silicate.

3. The process of claim 2 wherein said crystalline alumino silicate is ion exchanged with a metal ion or a hydrogen ion.

4. The process of claim 2 wherein said ion is selected from the group consisting of a trivalent metal ion, copper, and hydrogen.

5. The process of claim 2 wherein said olefin is a monounsaturated olefin having alpha-beta unsaturation.

6. The process of claim 5 wherein said primary and secondary amine of said nitrogen compound is a C₁₋₆ alkyl amine or cyclohexylamine.

7. The process of claim 5 wherein said nitrogen compound is ammonia.

8. The process of claim 7 wherein the pressure in said amination is from 300-6000 psig.

9. The process of claim 8 wherein the temperature in said amination is from 200°-450° C.

10. The process of claim 9 wherein the mole feed ratio of ammonia to olefin is from about 0.2-20:1.

11. The process of claim 10 wherein said alumino silicate exchanging ion is selected from the group consisting of a trivalent rare earth ion and hydrogen ion.

12. The process of claim 3 wherein said monounsaturated olefin is a straight chain C₂-C₄ monounsaturated olefin.

13. The process of claim 12 wherein the alumino silicate is zeolite Y or a mordenite.

14. The process of claim 13 wherein said olefin is selected from the group consisting of ethylene and propylene.

15. The process of claim 14 wherein said temperature is from 300°-400° C. and the pressure is from 600-1100 psig.

16. The process of claim 15 wherein the mole ratio of ammonia to olefin is from 1-10:1.

17. The process of claim 16 wherein said metal ion is a lanthanum ion.

18. The process of claim 3 wherein said olefin is cyclohexene.

19. The process of claim 18 wherein said crystalline alumino silicate is a zeolite Y or mordenite exchanged with a trivalent rare earth metal ion or hydrogen ion.

20. The process of claim 19 wherein said temperature is from 200°-400° C., said pressure is from 600-1100 psig and the ammonia to olefin mole ratio is from 1-10:1.

21. The process of claim 1 wherein said alumino-silicate is an acidic, synthetic alumino silicate.

22. A method of making amines which comprises contacting a mono-1-olefin having from 2-4 carbon atoms and ammonia in the vapor phase, with an acidic, synthetic crystalline alumino silicate under amination conditions which include a temperature in the range of from about 200° C. to 450° C., a pressure in the range of from about 300 to 1500 psig, a mole ratio of ammonia to olefin of about 1:10 and a gas hourly space velocity of about 500 to 5000.

23. The method of claim 22 wherein said alumino silicate has acidity provided by rare earth ions or hydrogen ions.

* * * * *

UNITED STATES PATENT AND TRADEMARK OFFICE
CERTIFICATE OF CORRECTION

PATENT NO. : 4,307,250
DATED : December 22, 1981
INVENTOR(S) : John O. H. Peterson et al It is certified that error appears in the above-identified patent and that said Letters Patent are hereby corrected as shown below:

Column 10, Table 6, Run 14
After 89 under "Other", insert -- acetonitrile--.

Signed and Sealed this

Twenty-first Day of September 1982

[SEAL]

Attest:

Attesting Officer

GERALD J. MOSSINGHOFF

Commissioner of Patents and Trademarks